United States Patent
Ju et al.

(10) Patent No.: US 11,182,923 B2
(45) Date of Patent: Nov. 23, 2021

(54) METHOD, COMPUTING DEVICE, AND SYSTEM FOR MONITORING POSTURES

(71) Applicant: Wistron Corporation, New Taipei (TW)

(72) Inventors: Ting-Feng Ju, New Taipei (TW); Chan-Hsuan Yu, New Taipei (TW); Kuo-Hsien Lu, New Taipei (TW)

(73) Assignee: Wistron Corporation, New Taipei (TW)

(*) Notice: Subject to any disclaimer, the term of this patent is extended or adjusted under 35 U.S.C. 154(b) by 108 days.

(21) Appl. No.: 16/508,331

(22) Filed: Jul. 11, 2019

(65) Prior Publication Data
US 2020/0302635 A1 Sep. 24, 2020

(30) Foreign Application Priority Data
Mar. 22, 2019 (TW) .................................. 108110000

(51) Int. Cl.
*G06T 7/70* (2017.01)
*G08B 21/04* (2006.01)

(52) U.S. Cl.
CPC ...... *G06T 7/70* (2017.01); *G06T 2207/10016* (2013.01); *G06T 2207/30196* (2013.01); *G06T 2207/30232* (2013.01); *G08B 21/0446* (2013.01)

(58) Field of Classification Search
None
See application file for complete search history.

(56) References Cited

U.S. PATENT DOCUMENTS

| 10,600,204 B1 * | 3/2020 | Rush .................... G06T 7/74 |
| 2019/0122039 A1 | 4/2019 | Chen et al. |

FOREIGN PATENT DOCUMENTS

| CN | 104545933 | 4/2015 |
| CN | 108629300 | 10/2018 |
| TW | M480134 | 6/2014 |
| TW | I637354 | 10/2018 |

OTHER PUBLICATIONS

"Office Action of Taiwan Counterpart Application," dated Feb. 4, 2020, p. 1-p. 7.

* cited by examiner

*Primary Examiner* — Leon Flores
(74) *Attorney, Agent, or Firm* — JCIPRNET

(57) ABSTRACT

A method, a computing device, and a system for monitoring postures are proposed. The method includes the following steps. An image sequence captured on a monitored area including a monitored subject is received. A first stable value corresponding to a first stage of stability of the monitored subject is detected, where the first stable value is associated with a position corresponding to a posture of the monitored subject remaining consecutively stable within a first predetermined time period. A second stable value corresponding to a second stage of stability of the monitored subject is detected, where the second stable value is associated with a position corresponding to a posture of the monitored subject remaining consecutively stable within a second predetermined time period. The first stable value and the second stable value are compared to accordingly determine whether a posture of the monitored subject has changed.

20 Claims, 7 Drawing Sheets

METHOD, COMPUTING DEVICE, AND SYSTEM FOR MONITORING POSTURES

CROSS-REFERENCE TO RELATED APPLICATION

This application claims the priority benefit of Taiwan application serial no. 108110000, filed on Mar. 22, 2019. The entirety of the above-mentioned patent application is hereby incorporated by reference herein and made a part of this specification.

TECHNICAL FIELD

The disclosure relates to a monitoring technique, in particular, to a method, a computing method, and a system for monitoring postures.

BACKGROUND

Bedsores, also known as pressure ulcers, are induced by prolonged pressure on skin and underlying tissues, leading to ischemic necrosis and ulceration. Bedsores commonly develop in individuals with the vegetative state or individuals not moving about such as those who are on chronic bedrest or with injuries to spinal cord. Hence, medical staffs are required to turn each patient at least every two hours to prevent bedsores. However, such basics could be potentially forgotten by the medical staffs due to their busy and tedious work tasks.

SUMMARY OF THE DISCLOSURE

Accordingly, a method, a computing method, and a system for monitoring postures are provided in the disclosure, where whether a posture of a monitored subject has changed is able to be effectively determined through image detection, thereby reducing costs and workload of manual monitoring.

According to one of the exemplary embodiments, the method is applicable to a computing device and includes the following steps. An image sequence associated with a monitored area is received, where the monitored area includes a monitored subject. A first stable value corresponding to a first stage of stability of the monitored subject is obtained, where the first stable value is associated with a position corresponding to a posture of the monitored subject remaining consecutively stable within a first predetermined time period. A second stable value corresponding to a second stage of stability of the monitored subject is obtained, where the second stable value is associated with a position corresponding to a posture of the monitored subject remaining consecutively stable within a second predetermined time period. The first stable value and the second stable value so as to accordingly determine whether a posture of the monitored subject has changed is compared.

According to one of the exemplary embodiments, the computing device includes a memory and a processor, where the processor is coupled to the memory. The memory is configured to store images and data. The processor is configured to receive an image sequence associated with a monitored area including a monitored subject, obtain a first stable value corresponding to a first stage of stability of the monitored subject, obtain a second stable value corresponding to a second stage of stability of the monitored subject, and compare the first stable value and the second stable value so as to accordingly determine whether a posture of the monitored subject has changed, where the first stable value is associated with a position corresponding to a posture of the monitored subject remaining consecutively stable within a first predetermined time period, and where the second stable value is associated with a position corresponding to a posture of the monitored subject remaining consecutively stable within a second predetermined time period.

According to one of the exemplary embodiments, the system includes an image capturing device and a computing device. The image capturing device is configured to capture an image sequence associated with a monitored area including a monitored subject. The computing device is configured to receive the image sequence from the image capturing device, obtain a first stable value corresponding to a first stage of stability of the monitored subject, obtain a second stable value corresponding to a second stage of stability of the monitored subject, and compare the first stable value and the second stable value so as to accordingly determine whether a posture of the monitored subject has changed, where the first stable value is associated with a position corresponding to a posture of the monitored subject remaining consecutively stable within a first predetermined time period, and where the second stable value is associated with a position corresponding to a posture of the monitored subject remaining consecutively stable within a second predetermined time period.

In order to make the aforementioned features and advantages of the present disclosure comprehensible, preferred embodiments accompanied with figures are described in detail below. It is to be understood that both the foregoing general description and the following detailed description are exemplary, and are intended to provide further explanation of the disclosure as claimed.

It should be understood, however, that this summary may not contain all of the aspect and embodiments of the present disclosure and is therefore not meant to be limiting or restrictive in any manner. Also, the disclosure would include improvements and modifications which are obvious to one skilled in the art.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

Figure 1:
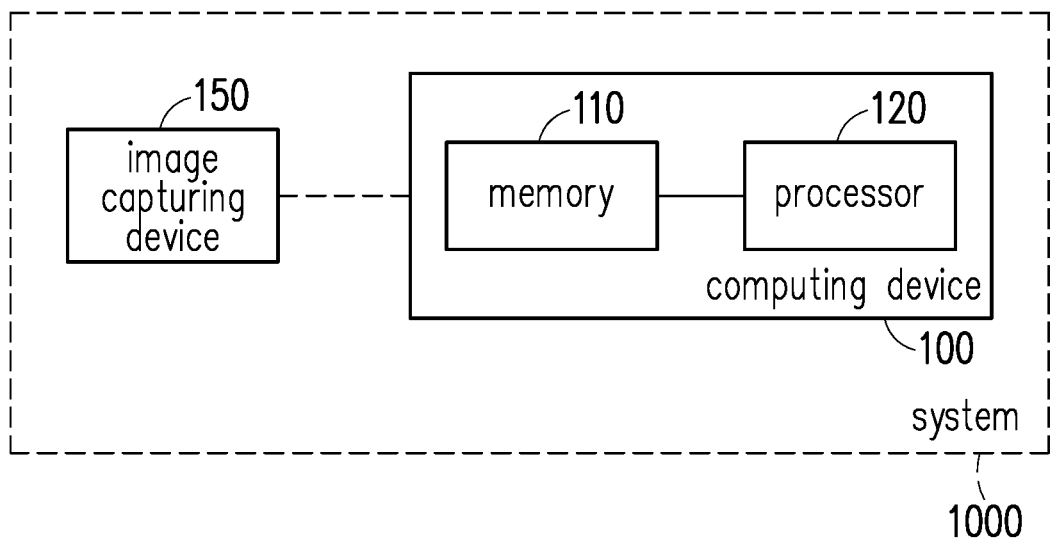
FIG. 1 illustrates a schematic block diagram of a system for monitoring postures in accordance with one of the exemplary embodiments of the disclosure.

To make the above features and advantages of the application more comprehensible, several embodiments accompanied with drawings are described in detail as follows.

DESCRIPTION OF THE EMBODIMENTS

Some embodiments of the disclosure will now be described more fully hereinafter with reference to the accompanying drawings, in which some, but not all embodiments of the application are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a schematic block diagram of a system for monitoring postures in accordance with one of the exemplary embodiments of the disclosure. All components of the mobile electronic device and their configurations are first introduced in FIG. 1. The functionalities of the components are disclosed in more detail in conjunction with FIG. 2.

In the present exemplary embodiment, a system 1000 for monitoring postures would include a computing device 100 and an image capturing device 150. The computing device 100 may be a personal computer, a laptop computer, a server computer, a tabular computer, a smart phone, a work station, or a computer system or a platform that is able to wired or wirelessly connected to the image capturing device 150 through a communication interface. The image capturing device 150 may be, for example, a digital camera, a digital camcorder, a web camera, or a surveillance camera. The communication interface may be a transmission interface that is compatible to any wired connection or wireless communication standard to transmit data with other devices. In another exemplary embodiment, the computing device 100 may be an embedded system that is built-in in the image capturing device 150 or that includes a built-in image capturing device 150, and the disclosure is not limited in this regard.

The memory 110 would be configured to store data such as images and programming codes and may be one or a combination of a stationary or mobile random access memory (RAM), a read-only memory (ROM), a flash memory, a hard drive, other similar devices or integrated circuits.

The processor 120 would be configured to control the operation among all the components of the computing device 100 and may be, for example, a central processing unit (CPU), a graphic processing unit (GPU) or other programmable devices for general purpose or special purpose such as a microprocessor and a digital signal processor (DSP), a programmable controller, an application specific integrated circuit (ASIC), a programmable logic device (PLD), other similar devices, a combination of above-mentioned devices or integrated circuits.

Detailed steps of how the computing device 100 in the system 1000 performs the method for monitoring postures would be illustrated along with each component in the exemplary embodiments hereafter.

Figure 2:
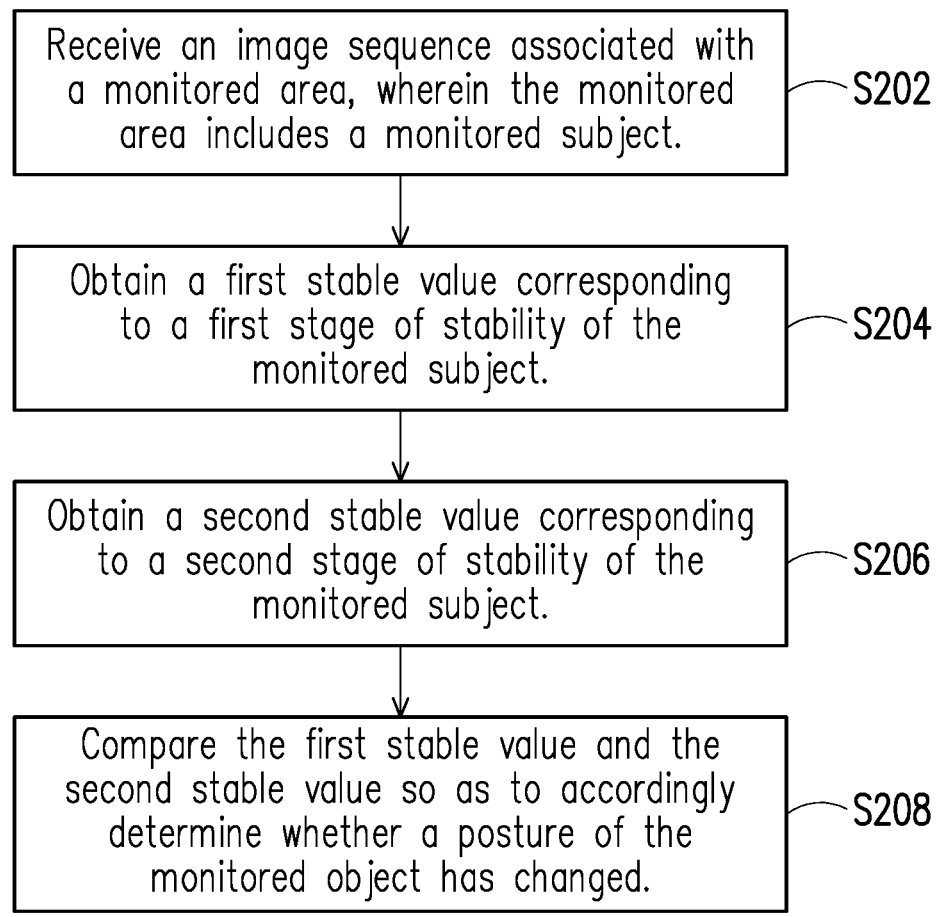
FIG. 2 illustrates a method for monitoring postures in accordance with one of the exemplary embodiments of the disclosure.

FIG. 2 illustrates a method for monitoring postures in accordance with one of the exemplary embodiments of the disclosure.

Referring to both FIG. 1 and FIG. 2, the processor 120 of the computing device 100 would receive an image sequence associated with a monitored area, where the monitored area would include a monitored subject (Step S202). In detail, the image capturing device herein may be mounted above the monitored area to continuously capture continuous image frames of the monitored area, and the captured continuous image frames would form the aforementioned "image sequence". In the following description, it is assumed that an angle of view of the image capturing device is fixed. However, the disclosure is not limited in this regard as the angle of view may be variated along with time or other different requirements. An application scenario of the present exemplary embodiment is nursing care, in which the image capturing device may be disposed above a bed in a home environment, a hospital or a care center for personal surveillance. In the present exemplary embodiment, the monitored area may be a part of a field of view of the image capturing device 150 such as the bed and its surroundings. In one exemplary embodiment, the monitored area may be set by obtaining an initial image captured by the image capturing device 150 in advance and displaying a user interface which may allow the user to define the position of the bed or the position of the bed and its surroundings from the initial image by ways of box selection or corner selection. The disclosure is not limited in this regard, though, in another exemplary embodiment, the monitored area may also be the entire field of view of the image capturing device 150. In the present exemplary embodiment, the monitored subject would be a patient on the bed. However, this is merely for illustration purposes, the disclosure is not limited in this regard.

Next, the processor 120 would obtain a first stable value corresponding to a first stage of stability of the monitored subject (Step S204). The first stage of stability herein may refer to a posture of the monitored subject remaining consecutively stable within a predetermined time period (referred to as "a first predetermined time period" hereafter), and the first stable value may refer to a position corresponding to the monitored subject within the first predetermined time period. In other words, the first stable value may be associated with the position corresponding to the posture of the monitored subject remaining consecutively stable within the first predetermined time period.

After the monitored subject reaches the first stage of stability, the processor 120 would obtain a second stable value corresponding to a second stage of stability of the monitored subject (Step S206). Similarly, the second stage of stability herein may refer to a posture of the monitored subject remaining consecutively stable within another predetermined time period (referred to as "a second predetermined time period" hereafter), and the second stable value may refer to a position corresponding to the monitored subject within the second predetermined time period. In other words, the second stable value may be associated with the position corresponding to the posture of the monitored subject remaining consecutively stable within the second predetermined time period.

Next, the processor 120 would compare the first stable value corresponding to the first stage of stability and the second stable value corresponding to the second stage of stability so as to accordingly determine whether the posture of the monitored subject has changed (Step S208). That is, the processor 120 may determine whether the posture of the monitored subject has changed by comparing the positions respectively corresponding to the posture of the monitored subject remaining consecutively stable within two predetermined time periods. When a difference between the first stable value and the second stable value is relatively large, this may indicate that there is a significant movement on the monitored subject, and therefore it may be assumed that the posture of the monitored subject has changed. When the difference between the first stable value and the second stable value is relatively small, this may indicate that the posture of the monitored subject has not changed.

Figure 3:
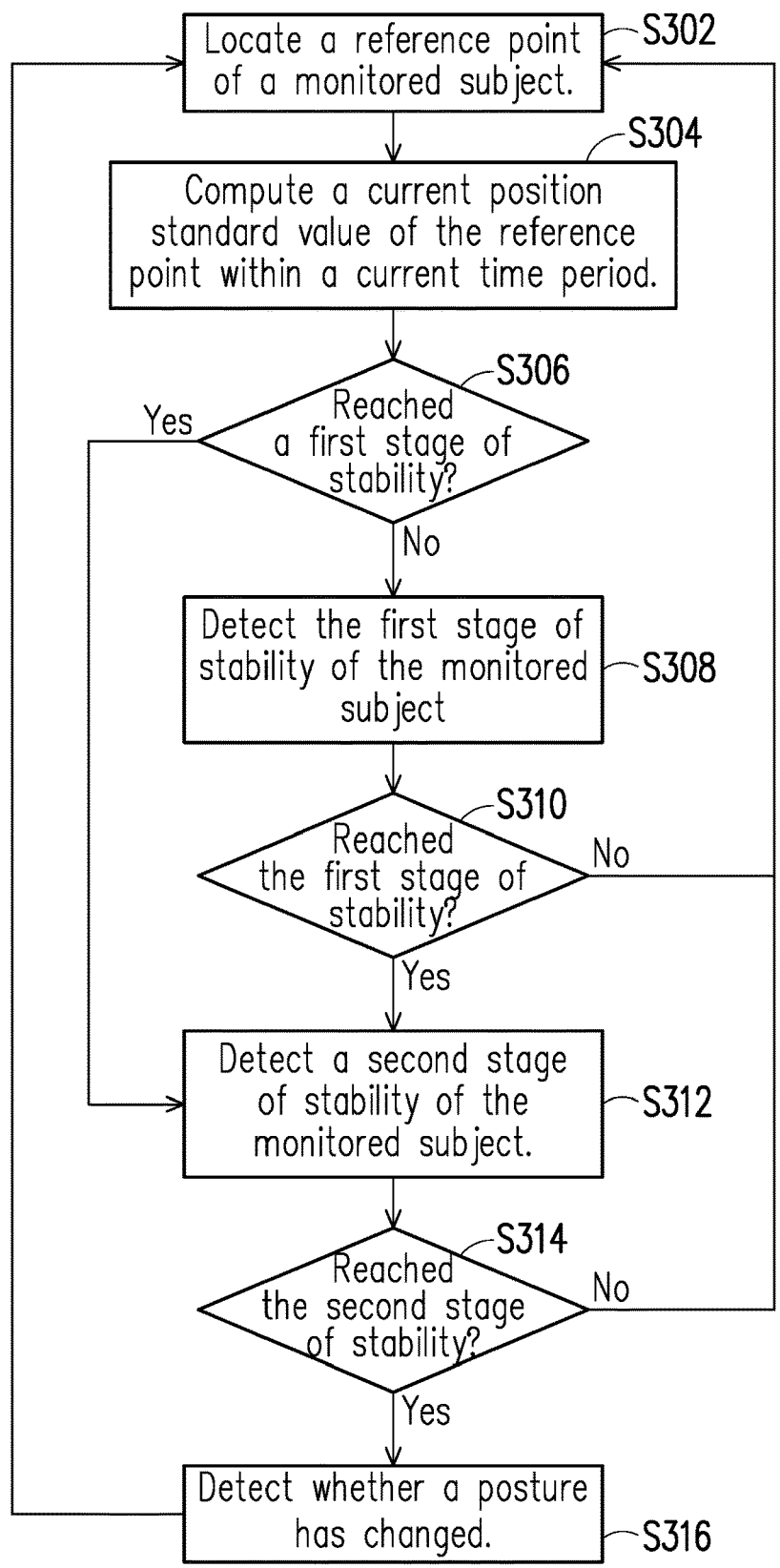
FIG. 3 illustrates a method for monitoring postures in accordance with one of the exemplary embodiments of the disclosure.

To be more comprehensive on the aforementioned flow, the details would be described as a flowchart of an application scenario of a method for monitoring postures as illustrated in FIG. 3 in accordance with one exemplary embodiments of the disclosure. In the present exemplary embodiment, a patient not moving about would be considered as the monitored subject, and any change of his posture would be caused by a medical staff's assistance with turning (i.e. repositioning). In such scenario, the processor 120 may confirm that the patient has been turned by the medical staff according to a change of stability within two time periods.

Referring to both FIG. 1 and FIG. 3, the processor 120 of the computing device 100 would locate a reference point of the monitored subject (Step S302). In the present exemplary embodiment, the reference point may represent a current position of the monitored subject, and the method for monitoring postures in the present exemplary embodiment may be performed by monitoring a position of the reference point. After the processor 120 locates the reference point of the monitored subject, it would compute a current position standard value of the reference point within a current time period (Step S304). Herein, the processor 120 may locate the reference point of the monitored subject from the image sequence, compute and set a position statistical value of the reference point within a currently-processed time period as the current position standard value for usage in the follow-up steps. The position statistical value herein may be an average position, a median position, and so forth, and yet disclosure is not limited in this regard.

In detail, the reference point in the present exemplary embodiment may be located at a chest of the monitored subject. The reason behind is that the chest is located at a core of a human body trunk and thus would have advantages such as more stable, not easily to be affected by the surroundings resulting in displacement, not easily to be affected by medical staffs' actions, not easily to be shaded, and so forth. Since the chest is minimally affected by ambient conditions, it may significantly represent a trend of posture changes. The disclosure is not limited in this regard, though, in other present exemplary embodiments, any other part of the monitored subject may also set as the reference point. In the present exemplary embodiment, the processor 220 may perform skeleton detection on the input frames in the image sequence by using the OpenPose library trained based on deep learning so as to label multiple coordinates of a body skeleton in each of the input frames including position coordinates of the chest, regardless whether the posture of the monitored subject is lying on his side or back. In the present exemplary embodiment, the reference point of the monitored subject may be located by using the position coordinate of the monitored subject's chest obtained through the OpenPose library. However, the disclosure is not limited in this regard as the reference point of the monitored subject may be located by using other algorithms in other exemplary embodiments.

In the present exemplary embodiment, an X direction and a Y direction would respectively represent a horizontal direction and a vertical direction of the field of view of the image capturing device 150. Assume that the bed and the horizontal direction (i.e. the X-direction) of the field of view of the image capturing device 150 are approximately perpendicular. The turning motion would mainly be the displacement with respect to the horizontal direction, and thus the processor 120 would only use an x-coordinate position of the chest for computation. As a side note, assume that the bed and the horizontal direction (i.e. the X-direction) of the field of view of the image capturing device 150 are approximately parallel in other exemplary embodiments. The turning motion would mainly be the displacement with respect to the vertical direction, and thus the processor 120 would only use a y-coordinate position of the chest for computation. In the present exemplary embodiment, since the coordinates obtained based on the result of the skeleton detection may be oscillated due to normal body shake or breathing rhythm, the processor 120 would compute an average of the x-coordinates of the reference point of input frames corresponding to a time period. The time period herein may be an empirical value such as 30 input frames. In terms of an image sequence filmed in 30 fps, the time period would then be 1 sec.

Figure 4:
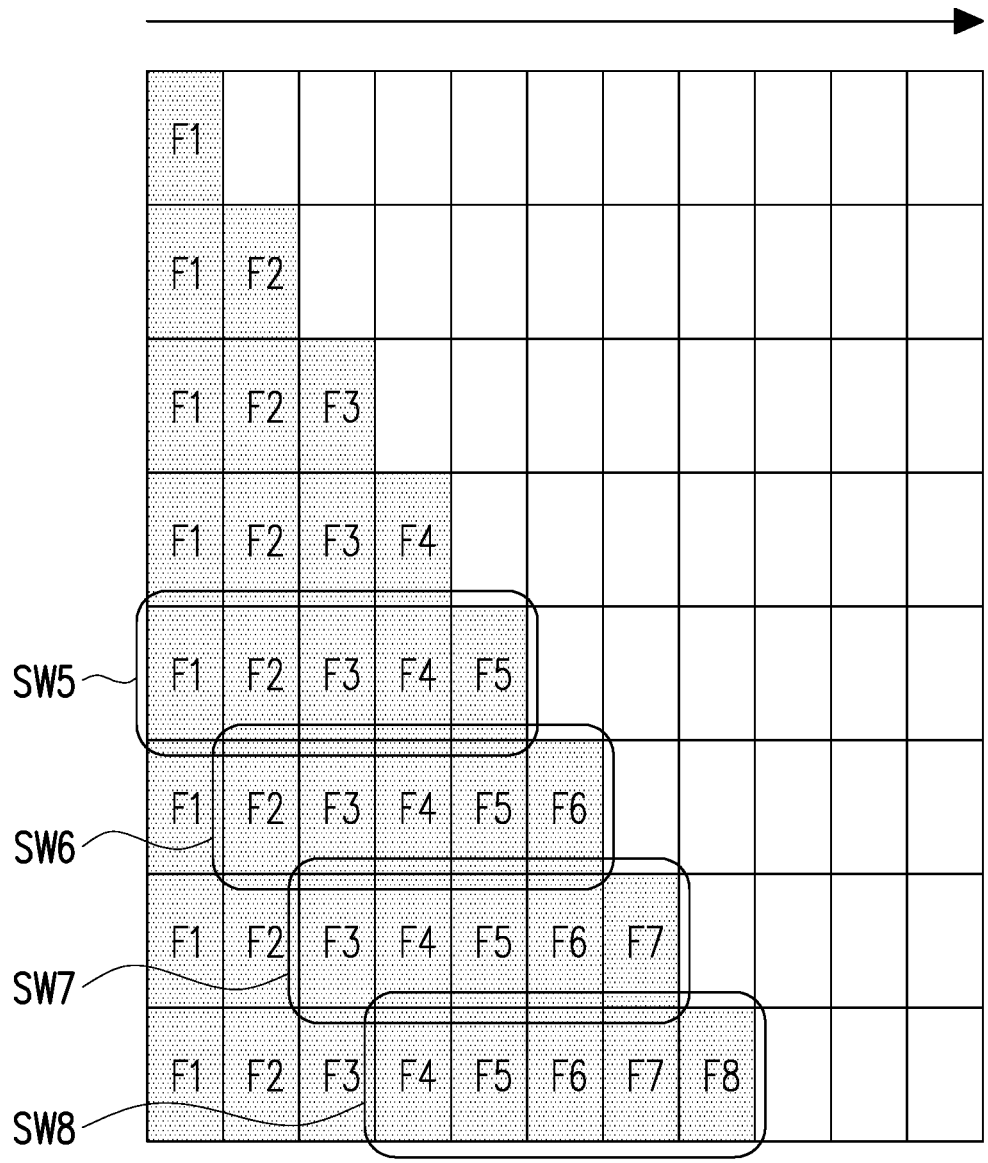
FIG. 4 illustrates a schematic diagram of an approach for calculating a position statistical value of a reference point in accordance with one of the exemplary embodiments of the disclosure.

To be specific, FIG. 4 illustrates a schematic diagram of an approach for calculating a position statistical value of a reference point in accordance with one of the exemplary embodiments of the disclosure. 5 input frames would be illustrated instead of 30 input frames hereafter for simplicity purposes.

Referring to FIG. 4, 5 input frames would be obtained by using a sliding window approach. Herein, when obtaining an input frame F5, the processor 120 would utilize the input frame F5 along with its previous 4 input frames F1-F4 within a sliding window SW5 to calculate a current position standard value CurrtA of a chest position (i.e. an average of x-coordinates of a reference point in the input frames F1-F5). When obtaining an input frame F6, the processor 120 would utilize the input frame F6 along with its previous 4 input frames F2-F5 within a sliding window SW6 to calculate a current position standard value CurrtA of the chest position (i.e. an average of x-coordinates of the reference point in the input frames F2-F6). Input frames F3-F7 within a sliding window SW7 and input frames F4-F8 within a sliding window SW8 may be deduced in a similar fashion.

Referring back to FIG. 3, the processor 120 would determine whether the monitored subject has reached the first stage of stability (Step S306). If the determination is negative, the processor 120 would detect the first stage of stability of the monitored subject (Step S308). Herein, the first stage of stability would represent the posture of the monitored subject remaining consecutively stable within a first predetermined time period, and the processor 120 would record all values including a first stable value ST1 in a stable condition. Details of Step S306 and Step S308 would be illustrated in FIG. 5 as a flowchart of a method for detecting a first stage of stability in accordance with one of the exemplary embodiments of the disclosure.

Figure 5:
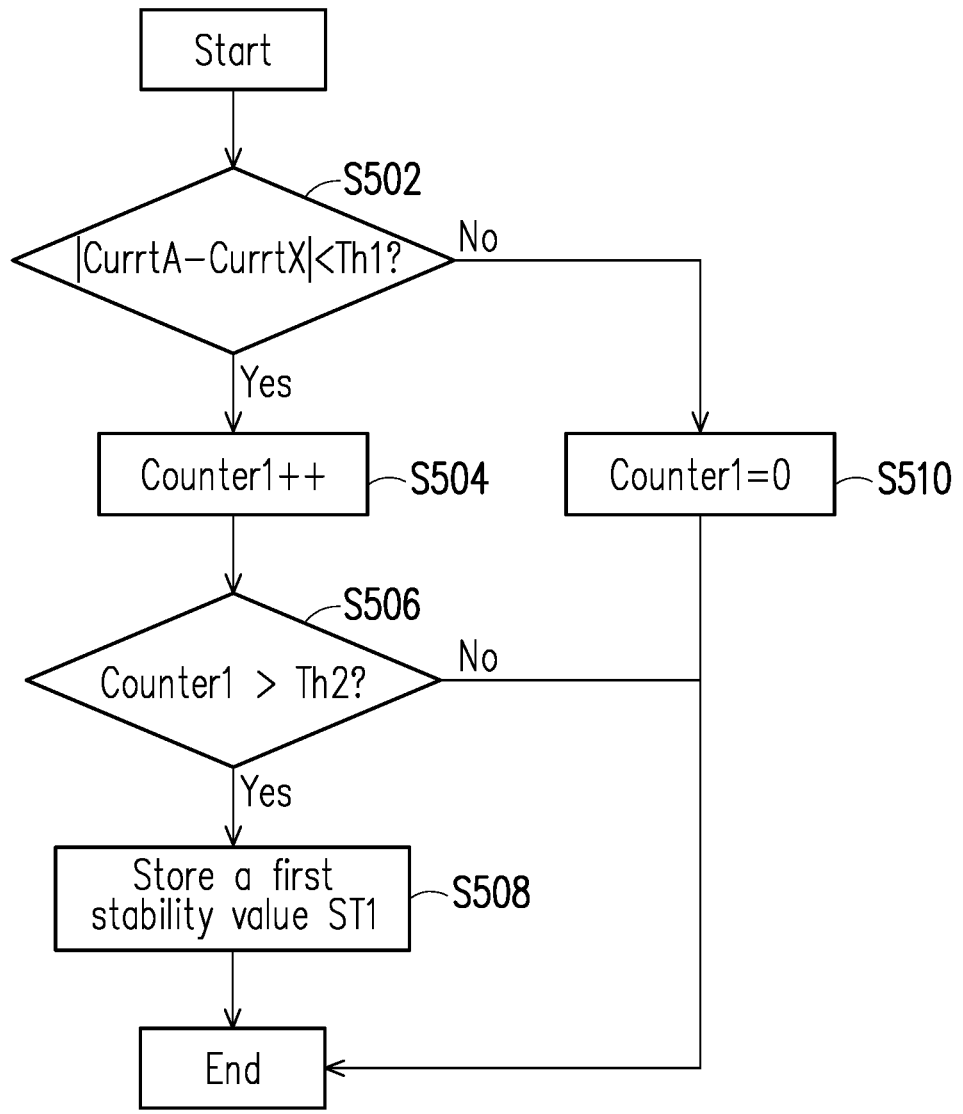
FIG. 5 illustrates a flowchart of a method for detecting a first stage of stability in accordance with one of the exemplary embodiments of the disclosure.

Referring to FIG. 5, when the processor 120 starts detecting a first stage of stability of a monitored subject, it would first determine whether a difference between a current position standard value CurrtA and a current position of a reference point CurrtX is less than a first threshold value Th1 (Step S502), where the first threshold value Th1 may be, for example, 30 pixels in a horizontal direction. Take FIG. 4 as an example. When obtaining the input frame F5, the processor 120 would determine whether a difference between a current position CurrtX$_5$ of the reference point in the input frame F5 and a current position standard value CurrtA$_{1-5}$ of the input frames F1-F5 is less than the first threshold value Th1. When obtaining the input frame F6, the processor 120 would determine whether a difference between a current position CurrtX$_6$ of the reference point in the input frame F6 and a current position standard value CurrtA$_{2-6}$ of the input frames F2-F6 is less than the first threshold value Th1. As a side note, the first threshold value Th1 would be the current position standard value CurrtA with plus and minus 30 pixels from another perspective, and therefore the processor 120 may also alternatively determine whether the current position CurrtX of the reference point is located within a tolerance range, between (CurrtA−30) and (CurrtA+30), where the first threshold value Th1 may avoid any false determination of instability due to normal body shake or breathing rhythm. Moreover, the first threshold value Th1 may be adjusted adaptively according to specifications and configuration conditions of the image capturing device 150. The disclosure is not limited in this regard.

When the processor 120 determines that the difference between the current position standard value CurrtA and the current position of a reference point CurrtX is less than the first threshold value Th1, this may represent that the current position of the reference point remains stable. The processor 120 would accumulate the number of counts to a first counter Counter1++ (Step S504). When the accumulated number of counts of stability is sufficient, i.e. when the first counter Counter1 is larger than a second threshold value Th2 (Step S506), this may indicate that the position of the reference point remains consecutively stable within a time period (e.g. the first predetermined time period). That is, the monitored subject has reached the first stage of stability. The second threshold Th2 herein may be 30 times. In other words, assume that a normal video frame rate is 30 fps. When a movement of the monitored subject remains less than the first threshold value Th1 for one second, the monitored subject would reach the first stage of stability. As a side note, the disclosure is not limited in this regard as the second threshold value Th2 may also be adjusted adaptively according to a turning speed of a medical staff. Next, the processor 120 would store the current position standard value CurrtA corresponding to first counter Counter1 being greater than the second threshold value Th2 as a first stable value ST1 (Step S508) and end the detection of the first stage of stability. On the other hand, during the accumulation, whenever the processor 120 determines that the difference between the current position standard value CurrtA and the current position of the reference point CurrtX is greater than the first threshold value Th1, this may indicate that the current position of the reference point CurrtX has a significant difference from the current position standard value CurrtA. That is, the position of the reference point is not stable enough, and thus the processor 120 would set the first counter to zero Counter1=0 (Step S510) and end the detection of the first stage of stability.

Referring back to FIG. 3, when ending the detection of the first stage of stability, the processor 120 would further determine whether the monitored subject has reached the first stage of stability (Step S310). If the determination is negative, it indicates that the first counter for the detection of the first stage of stability has been set to zero or has not yet reached the second threshold Th2. The processor 120 would return to Step S302 and process a next input frame to relocate the reference point of the monitored subject.

On the other hand, when determining that the monitored subject has reached the first stage of stability in Step S306 or Step S310, the processor 120 would detect a second stage of stability of the monitored subject (Step S312). Herein, the second stage of stability would represent the posture of the monitored subject remaining consecutively stable within a second predetermined time period, and the processor 120 would record all values including a second stable value ST2 in a stable condition. Step S312 would be similar to Step S308 and would be illustrated in FIG. 6 as a flowchart of a method for detecting a second stage of stability in accordance with one of the exemplary embodiments of the disclosure.

Figure 6:
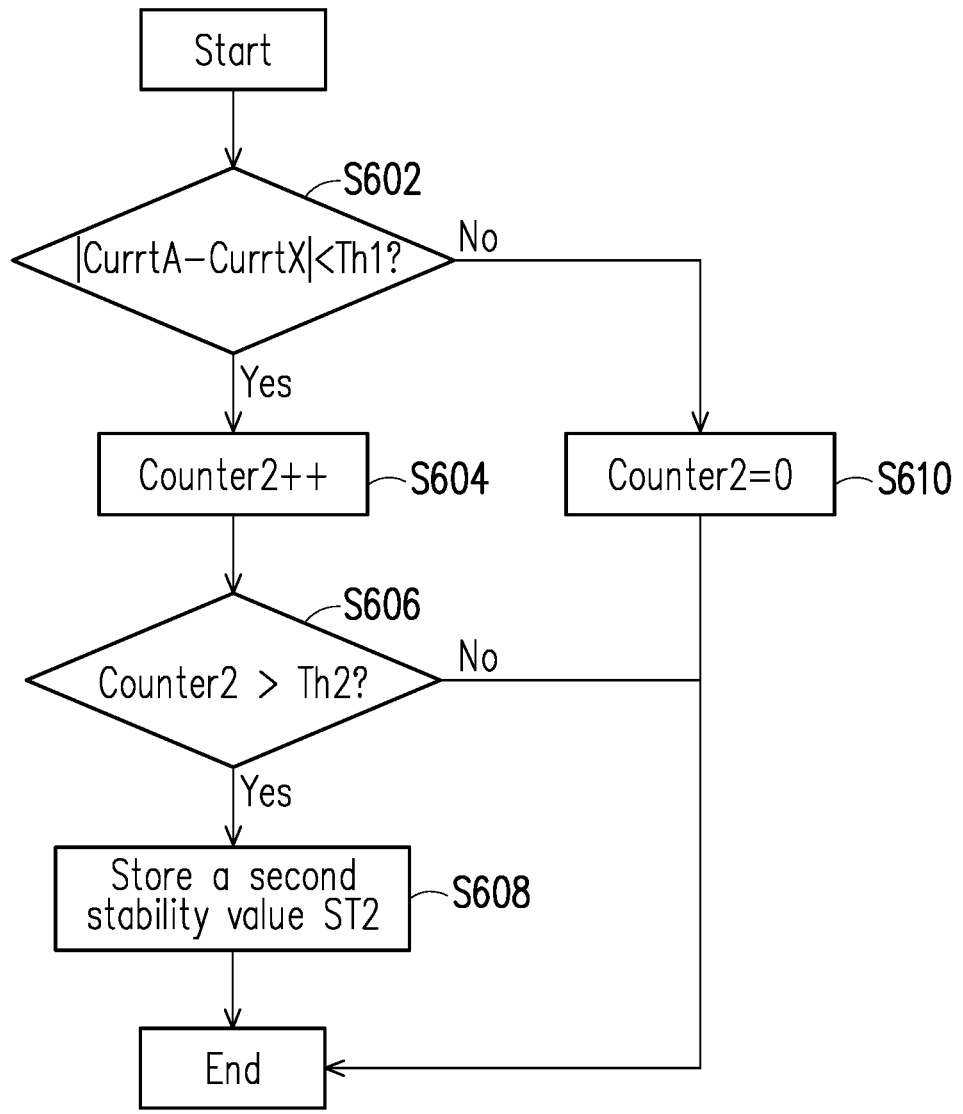
FIG. 6 illustrates a flowchart of a method for detecting a second stage of stability in accordance with one of the exemplary embodiments of the disclosure.

Referring to FIG. 6, when the processor 120 starts detecting a second stage of stability of a monitored subject, it would first determine whether a difference between a current position standard value CurrtA and a current position of a reference point CurrtX is less than a first threshold value Th1 (Step S602), where the first threshold value Th1 may also be, for example, 30 pixels in a horizontal direction. When determining that the difference between the current position standard value CurrtA and the current position of a reference point CurrtX is less than the first threshold value Th1, the processor 120 would accumulate the number of counts to a second counter Counter2++ (Step S604). When the accumulated number of counts of stability is sufficient, i.e. when the second counter Counter2 is larger than a second threshold value Th2 (Step S606), this may indicate that the position of the reference point remains consecutively stable within a time period (e.g. the second predetermined time period). That is, the monitored subject has reached the second stage of stability. The second threshold Th2 herein may also be 30 times. Herein, the processor 120 would store the current position standard value CurrtA corresponding to second counter Counter2 being greater than the second threshold value Th2 as a second stable value ST2 (Step S608) and end the detection of the second stage of stability. On the other hand, during the accumulation, whenever the processor 120 determines that the difference between the current position standard value CurrtA and the current position of the reference point CurrtX is greater than the first threshold value Th1, this may indicate that the current position of the reference point CurrtX has a significant difference from the current position standard value CurrtA. That is, the position of the reference point may not stable enough, and thus the processor 120 would set the second counter to zero Counter2=0 (Step S610) and end the detection of the second stage of stability.

Referring back to FIG. 3, when ending the detection of the second stage of stability, the processor 120 would determine whether the monitored subject has reached the second stage of stability (Step S314). If the determination is negative, it may indicate that the second counter for the detection of the second stage of stability has been set to zero or has not yet reached the second threshold Th2. The processor 120 would return to Step S302 and process a next input frame to relocate the reference point of the monitored subject.

On the other hand, when the processor 120 determines that the monitored subject has reached the second stage of stability, this may indicate that the processor 120 has obtained the first stable value corresponding to the first stage of stability as well as the second stable value corresponding to the second stage of stability. Therefore, the processor 120 would determine whether the posture of the monitored subject has changed (Step S316) and return to Step S302 regardless whether or not the posture of the monitored subject has changed for continuous monitoring. Details of Step S316 would be illustrated in FIG. 7 as a flowchart of a method for detecting posture changes in accordance with one of the exemplary embodiments of the disclosure.

Figure 7:
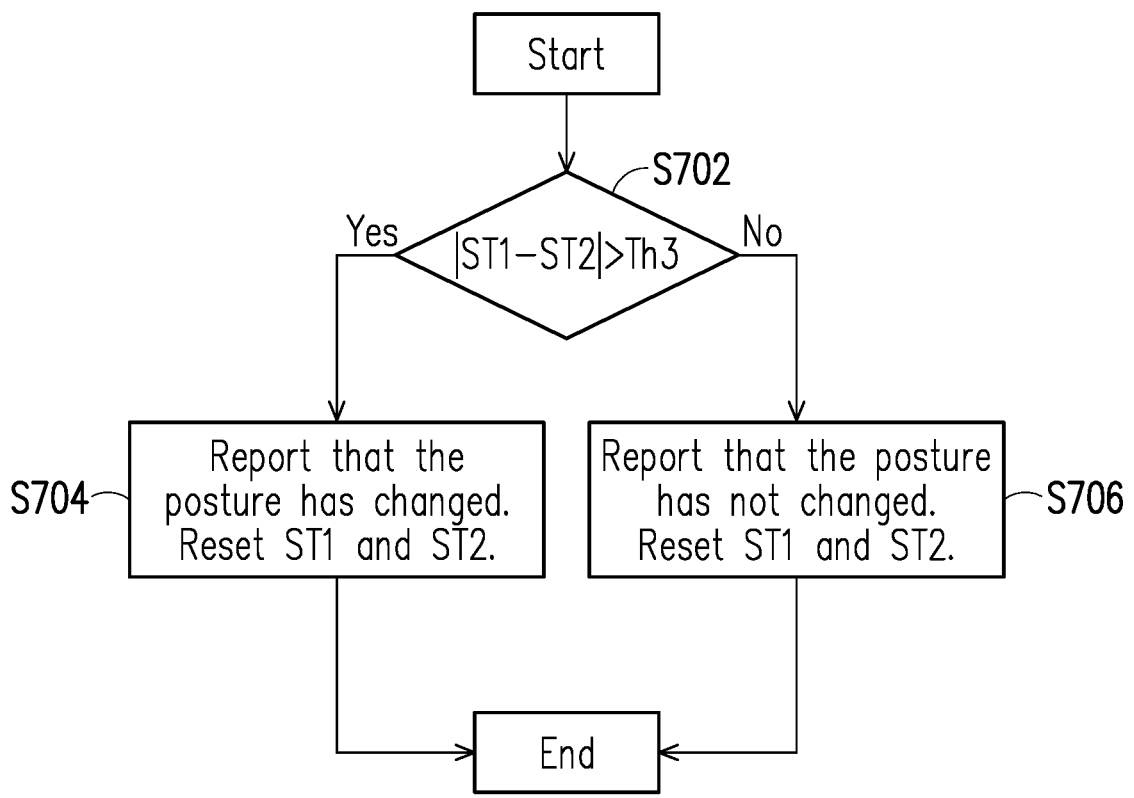
FIG. 7 illustrates a flowchart of a method for detecting posture changes in accordance with one of the exemplary embodiments of the disclosure.

Referring to FIG. 7, the processor 120 would determine whether a difference between a first stable value ST1 corresponding to a first stage of stability and a second stable value ST2 corresponding to a second stage of stability is greater than a third threshold value Th3 (Step S702), where the third threshold value Th3 should be greater than the first threshold value Th1 which is used to avoid any false determination due to normal body shake or breathing rhythm. As such, any positional movement of the monitored subject caused by his normal body shake or breathing rhythm would be prevented from being falsely determined to be posture changes. For example, the third threshold value Th3 may be, for example, 50 pixels in a horizontal direction. In detail, the first stable value ST1 and the second stable value ST2 may be average positions of the reference point respectively within different time periods. When the difference between the two is too large, this may indicate that the position of the reference point may have a significant movement. That is, the posture of the monitored subject has changed. Particularly, in the scenario of a patient not moving about to be the monitored subject, the reference point would be set at his chest, and a movement of the position of the chest would be caused by a medical staff's assistance with turning. Moreover, the third threshold value Th3 may also be set based on the degree of turning assisted by a medical staff.

When determining that the difference between the first stable value ST1 and the second stable value ST2 is greater than the third threshold value Th3, the processor 120 would determine and report that the posture of the monitored subject has changed and would reset the first stable value ST1 and the second stable value ST2 (Step S704). When determining that the difference between the first stable value ST1 and the second stable value ST2 is not greater than the third threshold value Th3, the processor 120 would determine and report that the posture of the monitored subject has not changed and would only reset the second stable value ST2 while keep the first stable value ST1 unchanged (Step S706).

In the present exemplary embodiment, the processor 120 may consider the report of the determination result of whether the posture of the monitored subject has changed as a record for tracking purposes. When the processor 120 has not received any report of the posture of the monitored subject having changed for a time period (referred to as "a third predetermined time period", e.g. 2 hours), the processor 120 would transmit a warning signal to a related system device where the medical staff is located or the medical staff's wearable device for notification to prevent the medical staff from forgetting to turn the patient due to busyness.

Figure 8:
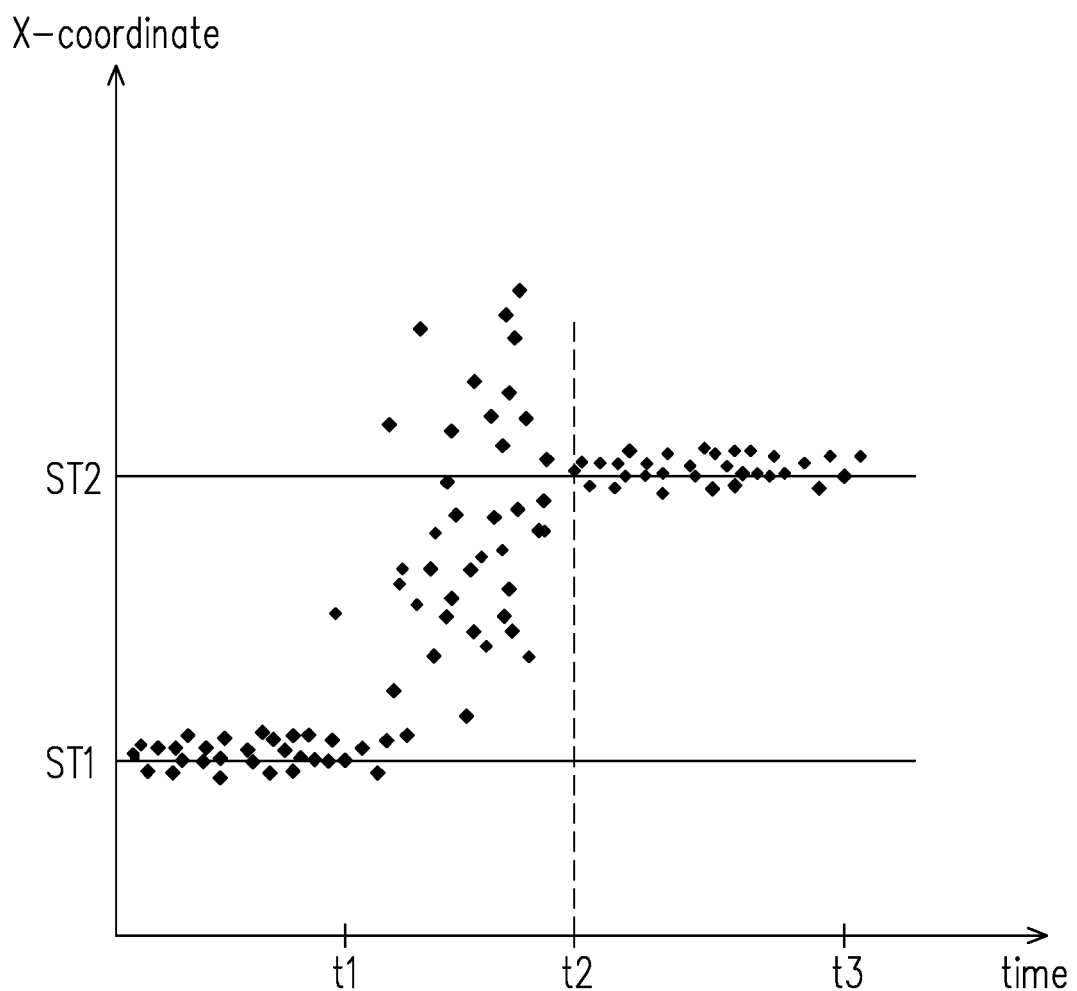
FIG. 8 illustrates a schematic diagram of a horizontal position coordinate of a chest at each timepoint in accordance with one of the exemplary embodiments of the disclosure.

To be more comprehensive, FIG. 8 illustrates a schematic diagram of a horizontal position coordinate of a chest at each timepoint in accordance with one of the exemplary embodiments of the disclosure.

Referring to FIG. 8 along with FIG. 3 and FIG. 5, the processor 120 would obtain a first stable value ST1 when the first stage of stability is reached at time t1. X-coordinates of the position of the chest between time t1 and time t2 would move drastically, where time t2 is a timepoint for turning. However, in terms of the processor 120, it would confirm that the patient has been turned after the second stage of stability is reached at time t2 and a difference between the first stable value ST1 and the second stable value ST2 is determined to be greater than 50 pixels.

In view of the aforementioned descriptions, in the method, the computing method, and the system for monitoring postures proposed in the disclosure, whether a posture of a monitored subject has changed would be able to effectively determined through image detection by comparing positions of the monitored subject corresponding to consecutive stabilities respectively within two predetermined time periods, thereby reducing costs and workload of manual monitoring.

No element, act, or instruction used in the detailed description of disclosed embodiments of the present application should be construed as absolutely critical or essential to the present disclosure unless explicitly described as such. Also, as used herein, each of the indefinite articles "a" and "an" could include more than one item. If only one item is intended, the terms "a single" or similar languages would be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for monitoring postures, applicable to a computing device, wherein the method comprises:
receiving an image sequence associated with a monitored area, wherein the monitored area comprises a monitored subject;
obtaining a first stable value corresponding to a first stage of stability of the monitored subject, wherein the first stable value is associated with a position corresponding to a posture of the monitored subject remaining consecutively stable within a first predetermined time period, and wherein a fluctuation of the position of the posture of the monitored subject within the first predetermined time period is less than a first threshold value;
obtaining a second stable value corresponding to a second stage of stability of the monitored subject, wherein the second stable value is associated with a position corresponding to a posture of the monitored subject remaining consecutively stable within a second predetermined time period which is after the first predetermined time period, and wherein a fluctuation of the position of the posture of the monitored subject within the second predetermined time period is less than the first threshold value; and
comparing the first stable value and the second stable value so as to accordingly determine whether a posture of the monitored subject has changed.

2. The method according to claim 1, wherein before the step of obtaining the first stable value corresponding to the first stage of stability of the monitored subject, the method further comprises:

locating a reference point of the monitored subject from the image sequence; and computing a current position standard value within a current time period, wherein the current position standard value is a position statistical value of the reference point within the current time period.

3. The method according to claim 2, wherein the reference point is located at a chest of the monitored subject.

4. The method according to claim 2, wherein after the step of computing the current position standard value within the current time period, the method further comprises:

determining whether the monitored subject has reached the first stage of stability;

in response that the monitored subject is determined not having reached the first stage of stability, detecting the first stage of stability of the monitored subject; and in response that the monitored subject is determined having reached the first stage of stability, detecting the second stage of stability of the monitored subject.

5. The method according to claim 4, wherein the step of detecting the first stage of stability of the monitored subject comprises:

determining whether a difference between the current position standard value and a current position of the reference point is less than the first threshold value;

in response that the difference between the current position standard value and the current position of the reference point is determined to be less than the first threshold value, accumulating a first counter and determining whether the first counter is greater than a second threshold value; and in response that the first counter is determined to be greater than the second threshold value, determining that the monitored subject has reached the first stage of stability.

6. The method according to claim 5, wherein in response that the monitored subject is determined having reached the first stage of stability, the method further comprises:

setting the current position standard value corresponding to the first counter being greater than the second threshold value as the first stable value.

7. The method according to claim 5 further comprising:

in response that the difference between the current position standard value and the current position of the reference point is determined to be not less than the first threshold value, setting the first counter to zero and determining that the monitored subject has not reached the first stage of stability; and in response that the first counter is not greater than the second threshold value, determining that the monitored subject has not reached the first stage of stability.

8. The method according to claim 4, wherein the step of detecting the second stage of stability of the monitored subject comprises:

determining whether a difference between the current position standard value and a current position of the reference point is less than the first threshold value;

in response that the difference between the current position standard value and the current position of the reference point is determined to be less than the first threshold value, accumulating a second counter and determining whether the second counter is greater than a second threshold value; and in response that the second counter is determined to be greater than the second threshold value, determining that the monitored subject has reached the second stage of stability.

9. The method according to claim 8, wherein in response that the monitored subject is determined having reached the second stage of stability, the method further comprises:

setting the current position standard value corresponding to the second counter being greater than the second threshold value as the second stable value.

10. The method according to claim 8 further comprising:

in response that the difference between the current position standard value and the current position of the reference point is determined to be not less than the first threshold value, setting the second counter to zero and determining that the monitored subject has not reached the second stage of stability; and in response that the second counter is not greater than the second threshold value, determining that the monitored subject has not reached the second stage of stability.

11. The method according to claim 1, wherein the step of comparing the first stable value and the second stable value so as to accordingly determine whether the posture of the monitored subject has changed comprises:

determining whether a difference between the first stable value and the second stable value is greater than a predefined threshold value;

in response that the difference between the first stable value and the second stable value is determined to be greater than the predefined threshold value, determining and reporting that the posture of the monitored subject has changed; and in response that the difference between the first stable value and the second stable value is determined to be not greater than the predefined threshold value, determining and reporting that the posture of the monitored subject has not changed.

12. The method according to claim 11 further comprising:

in response that the difference between the first stable value and the second stable value is determined to be greater than the predefined threshold value, resetting the first stable value and the second stable value; and in response that the difference between the first stable value and the second stable value is determined to be not greater than the predefined threshold value, resetting the second stable value; and in response that the posture of the monitored subject having changed has not been reported within a third predetermined time period, transmitting a warning signal.

13. A computing device comprising:

a memory, configured to store images and data;

a processor, coupled to the memory and configured to:

receive an image sequence associated with a monitored area, wherein the monitored area comprises a monitored subject;

obtain a first stable value corresponding to a first stage of stability of the monitored subject, wherein the first stable value is associated with a position corresponding to a posture of the monitored subject remaining consecutively stable within a first predetermined time period, and wherein a fluctuation of the position of the posture of the monitored subject within the first predetermined time period is less than a first threshold value;

obtain a second stable value corresponding to a second stage of stability of the monitored subject, wherein the second stable value is associated with a position corresponding to a posture of the monitored subject remaining consecutively stable within a second predetermined time period which is after the first predetermined time period, and wherein a fluctuation of the position of the posture of the monitored subject within the second predetermined time period is less than the first threshold value; and compare the first stable value and the second stable value so as to accordingly determine whether a posture of the monitored subject has changed.

14. The computing device according to claim 13, wherein the processor is further configured to:

locate a reference point of the monitored subject from the image sequence; and compute a current position standard value within a current time period, wherein the current position standard value is a position statistical value of the reference point within the current time period.

15. The computing device according to claim 14, wherein the reference point is located at a chest of the monitored subject.

16. The computing device according to claim 14, wherein the processor is further configured to:

determine whether the monitored subject has reached the first stage of stability;

in response that the monitored subject is determined not having reached the first stage of stability, detect the first stage of stability of the monitored subject; and in response that the monitored subject is determined having reached the first stage of stability, detect the second stage of stability of the monitored subject.

17. A system for monitoring postures comprising:

a camera, configured to capture an image sequence associated with a monitored area, wherein the monitored area comprises a monitored subject; and a computing device, comprising a processor configured to:

receive the image sequence from the camera;

obtain a first stable value corresponding to a first stage of stability of the monitored subject, wherein the first stable value is associated with a position corresponding to a posture of the monitored subject remaining consecutively stable within a first predetermined time period, and wherein a fluctuation of the position of the posture of the monitored subject within the first predetermined time period is less than a first threshold value;

obtain a second stable value corresponding to a second stage of stability of the monitored subject, wherein the second stable value is associated with a position corresponding to a posture of the monitored subject remaining consecutively stable within a second predetermined time period which is after the first predetermined time period, and wherein a fluctuation of the position of the posture of the monitored subject within the second predetermined time period is less than the first threshold value; and compare the first stable value and the second stable value so as to accordingly determine whether a posture of the monitored subject has changed.

18. The system according to claim 17, wherein the processor is further configured to:

locate a reference point of the monitored subject from the image sequence; and compute a current position standard value within a current time period, wherein the current position standard value is a position statistical value of the reference point within the current time period.

19. The system according to claim 18, wherein the reference point is located at a chest of the monitored subject.

20. The system according to claim 18, wherein the processor is further configured to:

determine whether the monitored subject has reached the first stage of stability;

in response that the monitored subject is determined not having reached the first stage of stability, detect the first stage of stability of the monitored subject; and in response that the monitored subject is determined having reached the first stage of stability, detect the second stage of stability of the monitored subject.

* * * * *